United States Patent
Straub et al.

(10) Patent No.: US 6,610,317 B2
(45) Date of Patent: Aug. 26, 2003

(54) POROUS PACLITAXEL MATRICES AND METHODS OF MANUFACTURE THEREOF

(75) Inventors: Julie Straub, Winchester, MA (US); Howard Bernstein, Cambridge, MA (US); Donald E. Chickering, III, Framingham, MA (US); Sarwat Khattak, Amherst, MA (US); Greg Randall, Somerville, MA (US)

(73) Assignee: Acusphere, Inc., Cambridge, MA (US)

( * ) Notice: Subject to any disclaimer, the term of this patent is extended or adjusted under 35 U.S.C. 154(b) by 0 days.

(21) Appl. No.: 09/798,824

(22) Filed: Mar. 2, 2001

(65) Prior Publication Data

US 2002/0041896 A1 Apr. 11, 2002

Related U.S. Application Data

(63) Continuation of application No. PCT/US00/14578, filed on May 25, 2000.
(60) Provisional application No. 60/186,310, filed on Mar. 2, 2000, provisional application No. 60/158,659, filed on Oct. 8, 1999, and provisional application No. 60/136,323, filed on May 27, 1999.

(51) Int. Cl.[7] .............................. A61F 2/00; A61F 9/14; A61F 31/335
(52) U.S. Cl. ...................... 424/422; 424/489; 424/426; 514/449
(58) Field of Search ................................. 424/422, 489, 424/426; 514/449

(56) References Cited

U.S. PATENT DOCUMENTS 5,855,913 A * 1/1999 Hanes et al. ................. 424/489
5,916,596 A * 6/1999 Desai et al. ................. 424/489

OTHER PUBLICATIONS

Waugh, "Stability, compatibility, and plasticizer extraction of taxol (NSC–125973) injection diluted in infusion solutions and stored in various containers, " *Am J Hosp Pharm* 48(7):1520–4 (1991).

* cited by examiner

Primary Examiner—Jose' G. Dees
Assistant Examiner—Robert M DeWitty
(74) Attorney, Agent, or Firm—Holland & Knight LLP

(57) ABSTRACT

Paclitaxel is provided in a porous matrix form, which allows the drug to be formulated without Cremophor and administered as a bolus. The paclitaxel matrices preferably are made using a process that includes (i) dissolving paclitaxel in a volatile solvent to form a paclitaxel solution, (ii) combining at least one pore forming agent with the paclitaxel solution to form an emulsion, suspension, or second solution, and (iii) removing the volatile solvent and pore forming agent from the emulsion, suspension, or second solution to yield the porous matrix of paclitaxel. The pore forming agent can be either a volatile liquid that is immiscible with the paclitaxel solvent or a volatile solid compound, preferably a volatile salt. In a preferred embodiment, spray drying is used to remove the solvents and the pore forming agent. In a preferred embodiment, microparticles of the porous paclitaxel matrix are reconstituted with an aqueous medium and administered parenterally, or processed using standard techniques into tablets or capsules for oral administration.

32 Claims, 1 Drawing Sheet

POROUS PACLITAXEL MATRICES AND METHODS OF MANUFACTURE THEREOF

This invention claims priority U.S. Ser. No. 60/186,310 filed Mar. 2, 2000, and is a continuation to PCT/US00/14578 filed May 25, 2000, which claims priority to U.S. Ser. No. 60/136,323 filed May 27, 1999, and U.S. Ser. No. 60/158,659 filed Oct. 8, 1999.

BACKGROUND OF THE INVENTION

This invention generally relates to formulations of paclitaxel and more particularly to methods of making formulations of paclitaxel.

Paclitaxel is a natural product which has been shown to possess cytotoxic and antitumor activity. Indeed, paclitaxel may be among the most active single agent for ovarian and breast cancers. This compound is found in small concentrations in the *Taxus brevifolia* species such as the Pacific yew tree among other Taxus species. While having an unambiguous reputation of tremendous therapeutic potential, paclitaxel as a therapeutic agent has some patient related drawbacks. These stem, in part, from its extremely low solubility in water, which makes it difficult to provide in suitable dosage form. Because of paclitaxel's poor aqueous solubility, the current approved clinical formulation consists of a 6 mg/ml solution of paclitaxel in 50% polyoxyethylated castor oil (CREMOPHOR EL™) and 50% dehydrated alcohol. *Am. J. Hosp. Pharm.*, 48:1520–24 (1991). In some instances, severe reactions, including hypersensitivity, occur in conjunction with the CREMOPHOR™ administered in conjunction with paclitaxel to compensate for its low water solubility. As a result of the incidence of hypersensitivity reactions to the commercial paclitaxel formulations and the potential for paclitaxel precipitation in the blood, the formulation must be infused over several hours. In addition, patients must be pretreated with steroids and antihistamines prior to the infusion.

In response to the hypersensitivity related to the CREMOPHOR™, the increasing recognition of paclitaxel's promise as an antineoplastic, and the undesirability of having to infuse the paclitaxel over several hours, there remains a need to develop improved formulations of the paclitaxel which can be administered as bolus injections.

It is therefore an object of the present invention to provide compositions of the paclitaxel without the solubilizing agent, CREMOPHOR™ which is present in the commercial formulation.

It is another object of the present invention to provide methods for producing the porous dry powder formulations of paclitaxel or docetaxol.

It is another object of the present invention to provide compositions providing enhanced dissolution of paclitaxel or docetaxol in a formulation suitable for administration by a variety of routes, including, but not limited to, parenteral, mucosal, oral, and topical administration, for local, regional, or systemic effect.

It is further object of the present invention to provide paclitaxel compositions for administration as a bolus injection instead of by infusion.

SUMMARY OF THE INVENTION

Paclitaxel is provided in a porous matrix form which forms nanoparticles and microparticles of paclitaxel when the matrix is contacted with an aqueous medium. The porous matrix with paclitaxel yields upon contact with an aqueous medium microparticles having a mean diameter between about 0.01 and 5 µm and a total surface area greater than about 0.5 m²/mL. The dry porous matrix is in a dry powder form having a TAP density less than or equal to 1.0 g/mL.

The porous matrices that contain the paclitaxel are preferably made using a process that includes (i) dissolving a paclitaxel in a volatile solvent to form a paclitaxel solution, (ii) combining at least one pore forming agent with the paclitaxel solution to form an emulsion, suspension, or second solution, and (iii) removing the volatile solvent and pore forming agent from the emulsion, suspension, or second solution to yield the dry porous matrix of paclitaxel. The resulting porous matrix has a faster rate of dissolution following administration to a patient, as compared to non-porous matrix forms of the paclitaxel. The pore forming agent can be either a volatile liquid that is immiscible with the paclitaxel solvent or a volatile solid compound, preferably a volatile salt. If the pore forming agent is a liquid, the agent is emulsified with the paclitaxel solution. If the pore forming agent is a solid, the agent is (i) dissolved in the paclitaxel solution, (ii) dissolved in a solvent that is not miscible in the paclitaxel solvent and then emulsified with the paclitaxel solution, or (iii) suspended as solid particulates in the paclitaxel solution. Optionally, hydrophilic excipients, wetting agents, and/or tonicity agents may be added to the paclitaxel solvent, the pore forming agent solvent, or both. The solution, emulsion, or suspension of the pore forming agent in the paclitaxel solution is then processed to remove the paclitaxel solvent and the pore forming agent, as well as any pore forming agent solvent. In a preferred embodiment, spray drying, optionally followed by lyophilization, fluid bed drying, or vacuum drying, is used to remove the solvents and the pore forming agent.

An advantage of the formulations is that they can be administered as a bolus, when the paclitaxel normally must be infused to avoid toxicity and to avoid precipitation of the drug. By avoiding precipitation of paclitaxel in vivo, the formulations can also be administered intrarterially, intravenously, locally, intracranially, intrathecally, or directly into a tumor. An additional advantage is the formulations can be administered in reduced volumes.

In one embodiment, the matrix further includes a pegylated excipient with the paclitaxel. The pegylated excipient shields the paclitaxel from macrophage uptake, which prolong its half-life or enhance bioavailability of the paclitaxel.

In a preferred embodiment, the porous paclitaxel matrix is reconstituted with an aqueous medium and administered parenterally, such as intramuscularly, subcutaneously, or intravenously. Alternatively, the porous paclitaxel matrix can be further processed using standard techniques into tablets or capsules for oral administration or into rectal suppositories, delivered using a dry powder inhaler for pulmonary administration, or mixed/processed into a cream or ointment for topical administration.

DETAILED DESCRIPTION OF THE INVENTION

Figure 1:
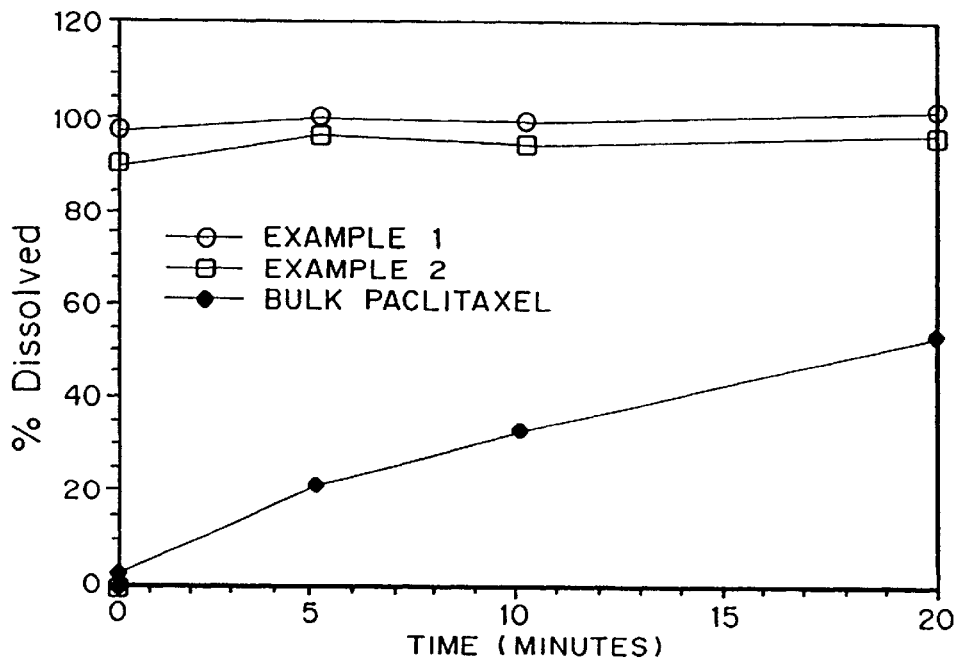
FIG. 1 is a graph of the in vitro dissolution rate (percent dissolved versus time) for non-formulated and various formulated paclitaxel in porous matrix form.

Compositions of paclitaxel without the solubilizing agent, CREMOPHOR™, and which can be administered as a bolus are disclosed. The compositions are porous dry powders, which upon the addition of an aqueous medium form a suspension of paclitaxel nanoparticles and microparticles. Methods for producing the formulations of paclitaxel include using pore forming agents. The compositions may contain hydrophilic excipients, such as water soluble polymers and sugars, and wetting agents, such as surfactants.

I. Paclitaxel Matrix Compositions

The porous paclitaxel matrix is at least 1 to 95%, preferably at least about 10%, and more preferably between about 10 and 70%, paclitaxel by weight. The matrices also may contain hydrophilic excipients such as water soluble polymers or sugars, wetting agents such as surfactants, and tonicity agents.

The matrix must yield microparticles of paclitaxel, upon contact with an aqueous medium which preferably have a diameter between about 10 nm and 5 μm, more preferably between about 50 nm and 5 μm. The average total surface area of the microparticles contained within the porous matrix, which typically is in the form of a dry powder, is 0.5 $m^2$/mL or greater. Total surface area values of the microparticles can be determined using standard particle sizing equipment and techniques.

The paclitaxel matrix must be sufficiently porous to yield microparticles, upon contact with an aqueous medium, having these parameters. Measurements useful in characterizing the porosity of the paclitaxel matrix are the bulk density or the transaxial pressure ("TAP") density of the dry porous matrix (dry powder) and the total surface area (sum of internal and external surface area) of the dry porous matrix. The TAP density preferably is less than about 1.0 g/ml, more preferably less than 0.8 g/ml. This level of porosity of the matrix, characterized by density, provides sufficient surface area to enhance wetting of the dry porous matrix and enhance paclitaxel dissolution.

The total surface area (sum of internal and external surface area) of the porous matrix can be measured, for example, by BET surface area analysis. In some embodiments, the total surface area of the porous matrix preferably is greater than 0.1 $m^2$/g, more preferably greater than or equal to 0.2 $m^2$/g. This level of total surface area provides sufficient surface area to enhance wetting of the dry porous matrix and enhance drug dissolution.

1. Paclitaxel

As generally used in the description herein, "paclitaxel" includes taxanes and derivatives thereof, including paclitaxel and docetaxel, which have anticancer or anti-angiogenic activity. Paclitaxel was specifically used in the examples which follow.

2. Excipients

The matrices may contain hydrophilic excipients, such as water soluble polymers or sugars, which can serve as bulking agents or as wetting agents, wetting agents such as surfactants or sugars, and tonicity agents. Upon contact with an aqueous medium, water penetrates through the highly porous matrix to dissolve the water soluble excipients in the matrix. A suspension of paclitaxel particles in the aqueous medium remains. The total surface area of the resultant low aqueous solubility paclitaxel microparticles is increased relative to the unprocessed paclitaxel and the dissolution rate of the paclitaxel is increased.

One of skill in the art can select appropriate excipients for use in the paclitaxel matrix compositions, considering a variety of factors, such as the paclitaxel to be administered, the route of administration, the dosage, and the preferred dissolution rate. For example, the excipients can function as bulking agents, release-modifiers, wetting agents, tonicity agents, or combinations thereof. Preferred excipients include hydrophilic polymers, wetting agents, and sugars. The amount of excipient in the paclitaxel matrix is less than about 95%, more preferably less than about 80%, by weight of the paclitaxel matrix.

The hydrophilic excipients, wetting agents, and tonicity agents may be added to the paclitaxel solution, the pore forming agent, or both, during production of the matrix.

(i) Hydrophilic Polymers

The polymers that can be used in the paclitaxel matrices described herein include both synthetic and natural polymers, either non-biodegradable or biodegradable. Representative synthetic polymers include polyethylene glycol ("PEG"), polyvinyl pyrrolidone, polymethacrylates, polylysine, poloxamers, polyvinyl alcohol, polyacrylic acid, polyethylene oxide, and polyethyoxazoline. Representative natural polymers include albumin, alginate, gelatin, acacia, chitosan, cellulose dextran, ficoll, starch, hydroxyethyl cellulose, hydroxypropyl cellulose, hydroxy-propylmethyl cellulose, hyaluronic acid, carboxyethyl cellulose, carboxymethyl cellulose, deacetylated chitosan, dextran sulfate, and derivatives thereof. Preferred hydrophilic polymers include PEG, polyvinyl pyrrolidone, poloxamers, hydroxypropyl cellulose, and hydroxyethyl cellulose.

The hydrophilic polymer selected for use in a particular paclitaxel matrix formulation is based on a variety of factors, such as the polymer molecular weight, polymer hydrophilicity, and polymer inherent viscosity. The hydrophilic polymer can be used as a bulking agent or as a wetting agent.

(ii) Sugars

Representative sugars that can be used in the paclitaxel matrices include mannitol, sorbitol, xylitol, glucitol, ducitol, inositiol, arabinitol, arabitol, galactitol, iditol, allitol, fructose, sorbose, glucose, xylose, trehalose, allose, dextrose, altrose, gulose, idose, galactose, talose, ribose, arabinose, xylose, lyxose, sucrose, maltose, lactose, lactulose, fucose, rhamnose, melezitose, maltotriose, and raffinose. Preferred sugars include mannitol, lactose, sucrose, sorbitol, trehalose, glucose, and are adjusted to provide osmolality if administered parenterally or to provide wetting of the porous paclitaxel matrix or the paclitaxel microparticles within the matrix.

(iii) Wetting Agents

Wetting agents can be used to facilitate water ingress into the matrix and wetting of the paclitaxel particles in order to facilitate dissolution.

Representative examples of wetting agents include gelatin, casein, lecithin (phosphatides), gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., TWEEN™s), polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethylcellulose phthlate, noncrystalline cellulose, magnesium aluminum silicate, triethanolamine, polyvinyl alcohol, and polyvinylpyrrolidone (PVP). Tyloxapol (a nonionic liquid polymer of the alkyl aryl polyether alcohol type, also known as superinone or triton) is another useful wetting agent. Most of these wetting agents are known pharmaceutical excipients and are described in detail in the Handbook of Pharmaceutical Excipients, published jointly by the American Pharmaceutical Association and The Pharmaceutical Society of Great Britain (The Pharmaceutical Press, 1986).

Preferred wetting agents include polyvinylpyrrolidone, polyethylene glycol, tyloxapol, poloxamers such as PLURONIC™ F68, F127, and F108, which are block copolymers of ethylene oxide and propylene oxide, and polyxamines such as TETRONIC™ 908 (also known as POLOXAMINE™ 908), which is a tetrafunctional block copolymer derived from sequential addition of propylene oxide and ethylene oxide to ethylenediamine (available from BASF), dextran, lecithin, dialkylesters of sodium sulfosuccinic acid such as AEROSOL™ OT, which is a dioctyl ester of sodium sulfosuccinic acid (available from American Cyanimid), DUPONOL™ P, which is a sodium lauryl sulfate (available from DuPont), TRITON™ X-200, which is an alkyl aryl polyether sulfonate (available from Rohm and Haas), TWEEN™ 20 and TWEEN™ 80, which are polyoxyethylene sorbitan fatty acid esters (available from ICI Specialty Chemicals), Carbowax 3550 and 934, which are polyethylene glycols (available from Union Carbide), CRODESTA™, which is a mixture of sucrose stearate and sucrose distearate, and CRODESTA™ SL-40 (both available from Croda Inc.), and SA90HCO, which is $C_{18}H_{37}CH_2(CON(CH_3)CH_2(CHOH)_4CH_2OH)_2$.

Wetting agents which have been found to be particularly useful include TETRONIC™ CRODESTA™ 908, the TWEENS™, PLURONIC™ F-68 and polyvinylpyrrolidone. Other useful wetting agents include decanoyl-N-methylglucamide; n-decyl-β-D-glucopyranoside; n-decyl-β-D-maltopyranoside; n-dodecyl-β-D-glucopyranoside; n-dodecyl β-D-maltoside; heptanoyl-N-methylglucamide; n-heptyl-β-D-glucopyranoside; n-heptyl-β-D-thioglucoside; n-hexyl-β-D-glucopyranoside; nonanoyl-N-methylglucamide; n-noyl-β-D-glucopyranoside; octanoyl-N-methylglucamide; n-octyl-β-D-glucopyranoside; and octyl-β-D-thioglucopyranoside. Another preferred wetting agent is P-isononylphenoxypoly(glycidol), also known as OLIN™-10G or Surfactant 10-G (commercially available as 10G from Olin Chemicals). Two or more wetting agents can be used in combination.

(iv) Tonicity or Osmolality Agents

The porous paclitaxel matrices may include one or more tonicity agents, such as salts (e.g., as sodium chloride or potassium chloride) or sugars (such as mannitol, dextrose, sucrose, or trehalose) to adjust a hypotonic solution of a paclitaxel to isotonic so that the paclitaxel, when in solution, is physiologically compatible with the cells of the body tissue of the patient. The type and amount of tonicity agent can be selected by one of skill in the art using known techniques.

(v) Pegylated Excipients

In one embodiment, the matrix further includes a pegylated excipient. Such pegylated excipients include, but are not limited to, pegylated phospholipids, pegylated proteins, pegylated peptides, pegylated sugars, pegylated polysaccharides, pegylated block co-polymers with of the blocks being PEG, and pegylated hydrophobic compounds such as pegylated cholesterol. The pegylated excipient beneficially envelops or shields the paclitaxel from macrophage uptake, which prolongs its half-life or enhances bioavailability of the paclitaxel.

Representative examples of pegylated phospholipids include 1,2-diacyl-sn-glycero-3-phosphoethanolamine-N-[Poly(ethyleneglycol) 2000] ("PEG 2000 PE") and 1,2-diacyl-sn-glycero-3-phosphoethanolamine-N-[Poly(ethylene glycol) 5000] ("PEG 5000 PE"), where the acyl group is selected, for example, from dimyristoyl, dipalmitoyl, distearoyl, diolcoyl, and 1-palmitoyl-2-oleoyl.

Other polyalkyleneoxides can be used in place of the polyethylene glycol.

II. Volatile Solvents

The choice of solvent depends on the paclitaxel. In a preferred embodiment, the solvent is an organic solvent that is volatile, has a relatively low boiling point, or can be removed under vacuum, and which is acceptable for administration to humans in trace amounts. Representative solvents include acetic acid, acetaldehyde dimethyl acetal, acetone, acetonitrile, chloroform, chlorofluorocarbons, dichloromethane, dipropyl ether, diisopropyl ether, N,N-dimethlyformamide (DMF), foramide, demethyl sulfoxide (DMSO), dioxane, ethanol, ethyl acetate, ethyl formate, ethyl vinyl ether, methyl ethyl ketone (MEK), glycerol, heptane, hexane, isopropanol, methanol, isopropanol, butanol, triethylamine, nitromethane, octane, pentane, tetrahydrofuran (THF), toluene, 1,1,1-trichloroethane, 1,1,2-trichloroethylene, water, xylene, and combinations thereof. In general, the paclitaxel is dissolved in the volatile solvent to form a paclitaxel solution having a concentration of between 0.01 and 80% weight to volume (w/v), more preferably between 0.025 and 30% (w/v).

Aqueous solvents or mixtures of aqueous and organic solvents, such as water-alcohol mixtures, can be used to dissolve the drug. In a preferred embodiment the volatile solvent is an aqueous mixture of an alcohol such as methanol or ethanol where the alcohol percent is in the range 40–100% (v/v).

III. Pore Forming Agents

Pore forming agents are volatile materials that preferably are used during the process to create porosity in the resultant matrix. The pore forming agent can be a volatilizable solid or volatilizable liquid.

1. Liquid Pore Forming Agent

The liquid pore forming agent must be immiscible with the paclitaxel solvent and volatilizable under processing conditions compatible with the paclitaxel. To effect pore formation, the pore forming agent first is emulsified with the paclitaxel solvent. Then, the emulsion is further processed to remove the paclitaxel solvent and the pore forming agent simultaneously or sequentially using evaporation, vacuum drying, spray drying, fluid bed drying, lyophilization, or a combination of these techniques.

The selection of liquid pore forming agents will depend on the paclitaxel solvent. Representative liquid pore forming agents include water; dichloromethane; alcohols such as ethanol, methanol, or isopropanol; acetone; ethyl acetate; ethyl formate; dimethylsulfoxide; acetonitrile; toluene; xylene; dimethylforamide; ethers such as THF, diethyl ether, or dioxane; triethylamine; foramide; acetic acid; methyl ethyl ketone; pyridine; hexane; pentane; furan; water; and cyclohexane.

The liquid pore forming agent typically is used in an amount that is between 1 and 50% (v/v), preferably between 5 and 25% (v/v), of the paclitaxel solvent emulsion.

2. Solid Pore Forming Agent

The solid pore forming agent must be volatilizable under processing conditions which do not harm the paclitaxel compositions. The solid pore forming agent can be (i) dissolved in the paclitaxel solution, (ii) dissolved in a solvent which is not miscible with the paclitaxel solvent to form a solution which is then emulsified with the paclitaxel solution, or (iii) added as solid particulates to the paclitaxel solution. The solution, emulsion, or suspension of the pore forming agent in the paclitaxel solution then is further processed to remove the paclitaxel solvent, the pore forming agent, and, if appropriate, the solvent for the pore forming agent simultaneously or sequentially using evaporation, spray drying, fluid bed drying, lyophilization, vacuum drying, or a combination of these techniques.

In a preferred embodiment, the solid pore forming agent is a volatile salt, such as salts of volatile bases combined with volatile acids. Volatile salts are materials that can transform from a solid or liquid to a gaseous state using added heat and/or vacuum. Examples of volatile bases include ammonia, methylamine, ethylamine, dimethylamine, diethylamine, methylethylamine, trimethylamine, triethylamine, and pyridine. Examples of volatile acids include carbonic acid, hydrochloric acid, hydrobromic acid, hydroiodic acid, formic acid, acetic acid, propionic acid, butyric acid, and benzoic acid. Preferred volatile salts include ammonium bicarbonate, ammonium acetate, ammonium chloride, ammonium benzoate and mixtures thereof.

Other examples of solid pore forming agents include iodine, phenol, benzoic acid (as acid not as salt), and naphthalene.

The solid pore forming agent is used in an amount between 0.5 and 1000% (w/w), preferably between 1 and 600% (w/w), and more preferably between 1 and 100% (w/w), of the paclitaxel.

IV. Method of Making the Porous Paclitaxel Matrix

The paclitaxel matrices preferably are made by (i) dissolving paclitaxel in a volatile solvent to form a paclitaxel solution, (ii) combining at least one pore forming agent with the paclitaxel solution to form an emulsion, suspension, or second solution, and (iii) removing the volatile solvent and pore forming agent from the emulsion, suspension, or second solution. In a preferred embodiment, spray drying, optionally followed by lyophilization or vacuum drying, is used to remove the solvents and the pore forming agent. The removal of the pore forming agent can be conducted simultaneously with or following removal of enough solvent to solidify the droplets. Production can be carried out using continuous, batch, or semi-continuous processes.

First, paclitaxel is dissolved in an appropriate solvent. The concentration of the paclitaxel in the resulting paclitaxel solution typically is between about 0.01 and 80% (w/v), preferably between about 0.025 and 30% (w/v).

Next, the paclitaxel solution is combined, typically under mixing conditions, with the pore forming agent or solution thereof. If a liquid pore forming agent is used, it is first emulsified with the paclitaxel solution to form droplets of pore forming agent dispersed throughout the paclitaxel solution. If a solid pore forming agent is used, it is dissolved either directly in the paclitaxel solution to form a solution of paclitaxel/pore forming agent, or it is first dissolved in a second solvent. If the second solvent is immiscible with the paclitaxel solvent, the solution of the pore forming agent is emulsified with the paclitaxel solution to form droplets of the pore forming agent solution dispersed throughout the paclitaxel solution. If the second solvent is miscible with the paclitaxel solution, the two solutions are mixed to form a single solution. A solid pore forming agent alternatively can be added directly to the paclitaxel solution as solid particulates, preferably between about 10 nm and 10 $\mu$m in size, to form a suspension of pore forming agent in the paclitaxel solution. Subsequently, the solid pore forming agent particle size can be reduced by further processing the resulting suspension, for example, using homogenization or sonication techniques known in the art.

Then, the solution, emulsion, or suspension is further processed to remove the paclitaxel solvent and the pore forming agent simultaneously or sequentially, using evaporation, spray drying, fluid bed drying, lyophilization, vacuum drying, or a combination of these techniques. In a preferred embodiment, the solution, emulsion, or suspension is spray-dried. As used herein, "spray dry" means to atomize the solution, emulsion, or suspension to form a fine mist of droplets (of paclitaxel solution having solid or liquid pore forming agent dispersed throughout), which immediately enter a drying chamber (e.g., a vessel, tank, tubing, or coil) where they contact a drying gas. The solvent and pore forming agents evaporate from the droplets into the drying gas to solidify the droplets, simultaneously forming pores throughout the solid. The solid (typically in a powder, particulate form) then is separated from the drying gas and collected.

The temperature of the inlet and outlet ports of the drying chamber, as well as the flow rates of the feed solution, atomization gas, and drying gas, can be controlled to produce the desired products. In a particularly preferred embodiment, the spray drying methods described in U.S. Pat. No. 5,853,698 to Straub et al., which is hereby incorporated by reference, are adapted to make the paclitaxel matrices described herein.

The paclitaxel present in the solids or powder produced may be in a crystalline or an amorphous state, or may be mixture of such states. The state generally depends on how the droplets are dried and the excipients present.

Emulsion Stabilization

In embodiments in which at least one pore forming agent is combined with the paclitaxel solution to form an emulsion, a surfactant or emulsifying agent can be added to enhance the stability of the emulsion. A variety of surfactants may be incorporated in this process, preferably to an amount between 0.1 and 5% by weight. Exemplary emulsifiers or surfactants which may be used include most physiologically acceptable emulsifiers, for instance egg lecithin or soya bean lecithin, or synthetic lecithins such as saturated synthetic lecithins, for example, dimyristoyl phosphatidyl choline, dipalmitoyl phosphatidyl choline or distearoyl phosphatidyl choline or unsaturated synthetic lecithins, such as dioleyl phosphatidyl choline or dilinoleyl phosphatidyl choline. Other hydrophobic or amphipathic compounds can be used in place of the phospholipid, for example, cholesterol. Emulsifiers also include surfactants such as free fatty acids, esters of fatty acids with polyoxyalkylene compounds like polyoxpropylene glycol and polyoxyethylene glycol; ethers of fatty alcohols with polyoxyalkylene glycols; esters of fatty acids with polyoxyalkylated sorbitan; soaps; glycerol-polyalkylene stearate; glycerol-polyoxyethylene ricinoleate; homo- and co-polymers of polyalkylene glycols; polyethoxylated soya-oil and castor oil as well as hydrogenated derivatives; ethers and esters of sucrose or other carbohydrates with fatty acids, fatty alcohols, these being optionally polyoxyalkylated; mono-, di- and tri-glycerides of saturated or unsaturated fatty acids, glycerides of soya-oil and sucrose.

Other emulsifiers include natural and synthetic forms of bile salts or bile acids, both conjugated with amino acids and unconjugated such as taurodeoxycholate and cholic acid.

V. Paclitaxel Matrix Applications

The paclitaxel matrices described herein are useful in formulations for administration to a patient in need of the paclitaxel. As used herein, "patient" refers to animals, including mammals, preferably humans. The porous matrices or formulations thereof are suitable for administration of the paclitaxel by a variety of routes, for example, parenteral, mucosal, oral, topical/transdermal administration, for local, regional, or systemic effect. Examples of parenteral routes include intravenous, intrarterial, intracardiac, intrathecal, intraosseous, intraarticular, intrasynovial, intracutaneous, subcutaneous, and intramuscular. Examples of mucosal routes include pulmonary (intrarespiratory), buccal, sublingual, intranasal, rectal, and vaginal administration. The porous matrices can be formulated for intraocular, conjunctival, aural, urethral, intracranial, intralesional, and intratumoral administration.

In a preferred embodiment, the paclitaxel matrix is in the form of powder, which can be reconstituted with an aqueous medium, such as physiological saline, and administered parenterally, such as intramuscularly, subcutaneously, or intravenously. An advantage of the formulations described herein is that they can be used to convert paclitaxel which must be infused (e.g., to avoid precipitation of the paclitaxel following bolus injection) to a bolus formulation, avoiding unacceptable precipitation of paclitaxel in vivo or for local delivery.

Alternatively, the matrix can be further processed using standard techniques into tablets or capsules for oral administration. These techniques are described, for example, in Ansel, et al., "*Pharmaceutical Dosage Forms and Paclitaxel Delivery Systems*," 6$^{th}$ Ed., (Williams & Wilkins 1995), which is incorporated herein by reference.

The present invention will be further understood with reference to the following non-limiting examples.

Overview

Examples 1–2 demonstrate production of paclitaxel matrices using different wetting agents and different solvents.

Examples 3–4 describe the analyses which were used to characterize the porous paclitaxel matrices produced in Examples 1–2. These characteristics include density and dissolution properties.

Example 6 describes the antitumor activity of the paclitaxel formulation produced in example 5 in female athymic NCr-nu mice in which the MDA-MB 435 breast tumor has been implanted subcutaneously (sc).

Materials and Equipment

The following materials and equipment were used in the examples. PEG 3350, polyvinylpyrrolidone K-15, TWEEN™ 80, and ammonium bicarbonate, were obtained from Spectrum Chemicals (Gardena, Calif.). Paclitaxel was obtained from Hauser (Boulder, Colo.). Methylene chloride was obtained from EM Science (Gibbstown, N.J.). All emulsions were produced using a Virtis IQ$^2$ homogenizer (Virtis, Gardiner, N.Y.). Formulations were spray dried on a benchtop spray dryer using an air atomizing nozzle.

Example 1

Production of a Porous Paclitaxel Matrix Using Ammonium Bicarbonate as a Pore Forming Agent A paclitaxel-loaded organic solution was prepared by dissolving 1.0 g of paclitaxel, 0.10 g of TWEEN™ 80, and 0.10 g of polyvinylpyrrolidone K-15 in 160 ml of ethanol. An aqueous solution composed of 0.42 g of ammonium bicarbonate and 1.0 g of mannitol in 40 ml of DI water was added to the ethanol solution and mixed. The resulting 80% ethanol solution was spray dried on a benchtop spray dryer using an air-atomizing nozzle and nitrogen as the drying gas. Spray drying conditions were as follows: 20 ml/min solution flow rate, 60 L/min atomization gas rate, 100 kg/hr drying gas rate, and 55° C. outlet.

Example 2

Production of a Porous Paclitaxel Matrix Using Ammonium Bicarbonate as a Pore Forming Agent A paclitaxel-loaded organic solution was prepared by dissolving 0.4 g of paclitaxel, 0.10 g of TWEEN™ 80, and 0.04 g of polyvinylpyrrolidone K-15 in 160 ml of ethanol. An aqueous solution composed of 0.30 g of ammonium bicarbonate and 1.0 g of mannitol in 40 ml of DI water was added to the ethanol solution and mixed. The resulting 80% ethanol solution was spray dried on a benchtop spray dryer using an air-atomizing nozzle and nitrogen as the drying gas. Spray drying conditions were as follows: 20 ml/min solution flow rate, 60 L/min atomization gas rate, 100 kg/hr drying gas rate, and 55° C. outlet temperature.

Example 3

In Vitro Dissolution of Porous Paclitaxel Matrices

The in vitro dissolution rates of the powders produced in Examples 1–2 were compared to the dissolution rates of the non-formulated paclitaxel.

Analytical Methods

Studies were conducted in PBS containing 0.08% TWEEN™ 80 (T80/PBS). T80/PBS (10 mL) was added to an appropriate amount of material being tested to contain 5 mg of paclitaxel in a 15 mL polypropylene conical tube, and the suspension was vortexed for 3–4 minutes. The suspension (0.25 mL) was then added to 250 mL of T80/PBS in a 600 mL glass beaker for dissolution analysis. All dissolution studies were conducted using overhead mixing. The mixer used was an IKARW16 Basic Mixer with a R1342 impeller shaft running at stirring rate 5. Samples were removed via pipette, filtered through 0.22 micron CA syringe filter, and then analyzed. Dissolution curves are presented as percent of complete dissolution.

HPLC analysis was performed directly on the filtered aqueous solutions using High Pressure Liquid Chromatography ("HPLC") (Hewlett Packard Series 1100 HPLC). The chromatographic conditions included a Nucleosil column (5:m, C18, 100A, 250×4.6 mm), a mobile phase of 2 mM $H_3PO_4$/Acetonitrile (2:3) at a flow rate of 1.5 mL/min, UV detection at 227 nm, and a run time of 25 min.

Results

The in vitro dissolution rates of the porous paclitaxel matrices produced in examples 1–2 are provided in FIG. 1. The in vitro dissolution of the porous paclitaxel matrices are compared to the bulk paclitaxel of interest. In all cases, the time for 80% dissolution of the porous paclitaxel matrices is greater than 1000 times shorter than the time for 80% of the bulk paclitaxel to dissolve. The rate of dissolution which is approximated as the slope of the curve is greater than 1000 times greater for the porous paclitaxel matrices of Examples 1–2 as compared to the specific bulk paclitaxel of interest.

Example 4

Density of Porous Paclitaxel Matrices

The densities of the dry powder produced in Examples 1–2 are summarized in Table 1. Density was measured using Transaxial Pressure ("TAP") with a Micromeritics GeoPyc 1360 using a consolidation force of 8 Newtons. The density of the porous matrices is less than 1.0 g/mL for Examples 1–2.

TABLE 1

Particle Density Analysis

| Material | Density (g/mL) |
|---|---|
| Example 1 | 0.67 |
| Example 2 | 0.52 |

Example 5

Production of a Porous Paclitaxel Matrix For Testing in Animal Tumor Model

A paclitaxel-loaded organic solution was prepared by dissolving 2.0 g of paclitaxel, 0.20 g of polyvinylpyrrolidone, and 0.20 g of TWEEN™ 80 in 320 ml of ethanol. An aqueous solution composed of 0.85 g of ammonium bicarbonate and 2.0 g of mannitol in 80 ml of DI water was added to the organic solution (phase ratio 1:4). Prior to spray drying, the solution was filtered through a 0.22 µm PVDF membrane. A benchtop spray dryer using an air-atomizing nozzle and nitrogen as the drying gas were used. Spray drying conditions were as follows: 20 ml/min solution flow rate, 60 L/min atomization gas rate, 100 kg/hr drying gas rate, and 54° C. outlet temperature.

Example 6

Testing of Porous Paclitaxel Matrix in Animal Efficacy Model

Figure 2:
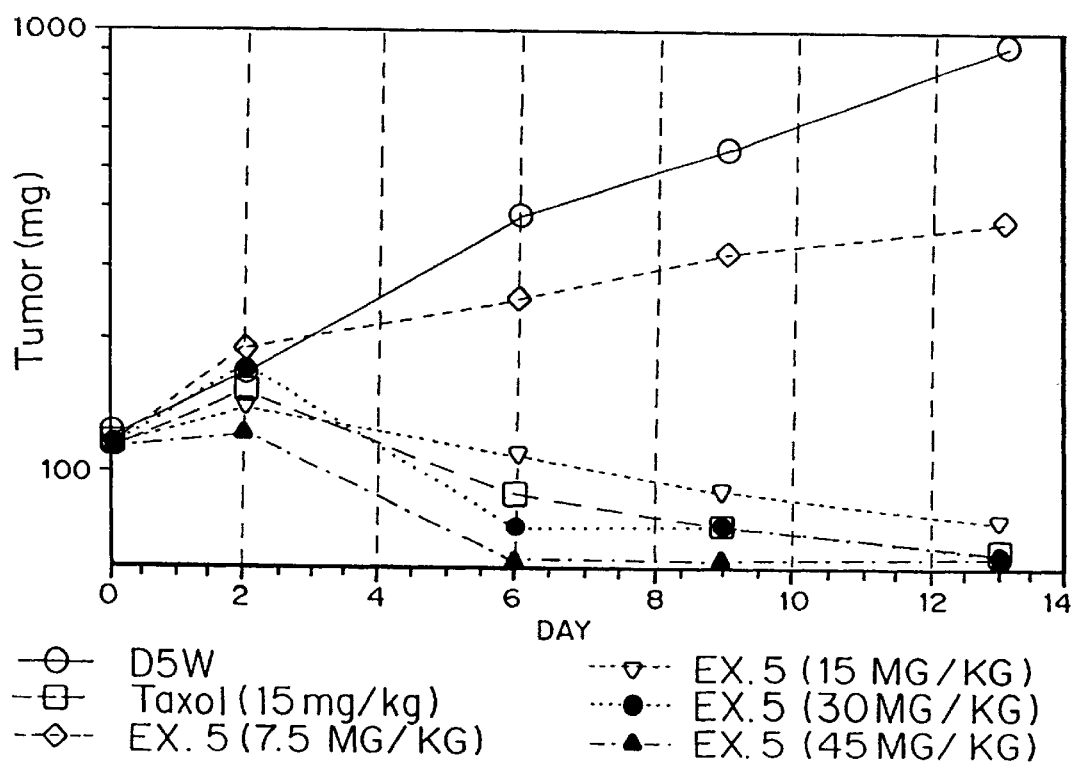
FIG. 2 is a graph of median MDA-MB 435 breast tumor weight in female athymic NCr-nu mice following five days of therapy with paclitaxel in porous matrix form.

The antitumor activity of the paclitaxel formulation produced in Example 5 was tested in female athymic NCr-nu mice in which the MDA-MB 435 breast tumor has been implanted subcutaneously (sc), using doses of 7.5, 15, 30, and 45 mg/kg. Mice were implanted subcutaneously with 30–40 mg fragments of the MDA-MB 435 tumor on Day 0. Treatment with the porous paclitaxel matrix began when the tumors ranged in size from 75–150 mg. Two control groups were included, a vehicle-treated control group and a TAXOL™ treated group. The dose of the TAXOL™ treated group was set at the maximum tolerated dose in this animal model. Treatment was administered once a day intravenously for five days. Mice were observed daily for survival. Tumor measurements were recorded twice weekly. Tumors were measured in two dimensions using calipers and converted to tumor mass using the volume of a prolate ellipsoid and assuming unit density. Median tumor mass for the various groups in shown in FIG. 2 plotted as a function of the day, with day 0 being the first day of dosing. There was no tumor regression in the dextrose vehicle control group. The administration of the porous paclitaxel matrix lead to a dose dependent regression in tumor mass with tumor masses below the limit of detection at the highest dose by day 6. The porous paclitaxel matrix therefore allows for elimination of Cremophor and ethanol and thus higher total doses of paclitaxel were administered. The higher dose porous paclitaxel matrix groups had a more rapid rate of tumor regression and smaller tumor mass.

Modifications and various of the present invention will be obvious to those of skill in the art from the foregoing detailed description. Such modifications and various are intended to come within the scope of the following claims.

We claim:
1. A pharmaceutical composition comprising
   a porous matrix formed of a hydrophilic excipient, a wetting agent and nanoparticles and microparticles of a taxane,
   wherein the nanoparticles and microparticles have a mean diameter between about 0.01 and 5 µm and a total surface area greater than about 0.5 m²/,
   wherein the porous matrix is in a dry powder form, and
   wherein upon exposure to an aqueous medium, the matrix dissolves to leave the taxane nanoparticles and microparticles, wherein the dissolution rate of the taxane nanoparticles and microparticles in an aqueous solution is increased relative to unprocessed taxane.
2. The composition of claim 1, wherein the matrix is made by a process comprising
   (a) dissolving a taxane in a volatile solvent to form a taxane solution,
   (b) combining at least one pore forming agent, a wetting agent, and a hydrophilic excipient with the taxane solution to form an emulsion, suspension, or second solution, and
   (c) removing the volatile solvent and the pore forming agent from the emulsion, suspension, or second solution to yield the porous matrix.
3. The composition of claim 2 wherein the pore forming agent is a volatile salt.
4. The composition of claim 1 wherein the porous matrix is in a dry powder form having a TAP density less than or equal to 1.0 g/mL.
5. The composition of claim 1, wherein the matrix comprises at least one excipient selected from the group consisting of hydrophilic polymers, sugars, tonicity agents, pegylated excipients, and combination thereof.
6. The composition of claim 1 wherein the mean diameter of the taxane microparticles is between about 0.50 and 5 µm.
7. A taxane suspension comprising the composition of claim 1 added to an aqueous solution suitable for parenteral administration.
8. The composition of claim 1 wherein the matrix is processed into tablets or capsules suitable for oral administration.
9. The composition of claim 1 wherein the matrix is formed into suppositories suitable for vaginal or rectal administration.
10. The composition of claim 1 wherein the matrix is in a dry powder form suitable for pulmonary administration.
11. A method for making a porous matrix of a taxane comprising
   (a) dissolving a taxane in a volatile solvent to form a taxane solution,
   (b) combining at least one pore forming agent, a wetting agent, and a hydrophilic excipient with the taxane solution to form an emulsion, suspension, or second solution, and
   (c) removing the volatile solvent and pore forming agent from the emulsion, suspension, or second solution to yield the porous matrix comprising nanoparticles and microparticles of taxane, wherein the dissolution rate of the taxane nanoparticles and microparticles in an aqueous solution is increased relative to unprocessed taxane.
12. The method of claim 11 wherein the wetting agent is a polyoxyethylene sorbitan fatty acid ester.
13. The method of claim 11 wherein step (c) is conducted using a process selected from spray drying, evaporation, fluid bed drying, lyophilization, vacuum drying, or a combination thereof.

14. The method of claim 11 wherein the taxane solution or pore forming agent comprises excipients selected from the group consisting of hydrophilic excipients, pegylated excipients, and tonicity agents.

15. The method of claim 11 wherein the pore forming agent is a volatile salt.

16. The method of claim 15 wherein the volatile salt is selected from the group consisting of ammonium bicarbonate, ammonium acetate, ammonium chloride, ammonium benzoate, and mixtures thereof.

17. A method of treating a patient with a taxane, comprising administering to a patient in need thereof a therapeutically or prophylactically effective amount of a taxane in a formulation comprising a porous matrix formed of a hydrophilic excipient, a wetting agent and nanoparticles and microparticles of a taxane, wherein the nanoparticles and microparticles have a mean diameter between about 0.01 and 5 $\mu$m and a total surface area greater than about 0.5 $m^2$/mL, and wherein the porous matrix is in a dry powder form having a TAP density less than or equal to 1.0 g/mL. wherein upon exposure to an aqueous medium, the matrix dissolves to leave the taxane nanoparticles and microparticles wherein the dissolution rare of the taxane nanoparticles and microparticles in an aqueous solution is increased relative to unprocessed taxane.

18. The method of claim 17 wherein the formulation is suitable for administration by a route selected from the group consisting of parenteral, mucosal, oral, and topical administration.

19. The method of claim 18 wherein the parenteral route is selected from the group consisting of intravenous, intraarterial, intracardiac, intrathecal, intraosseous, intraarticular, intrasynovial, intracutaneous, subcutaneous, and intramuscular administration.

20. The method of claim 18 wherein the mucosal route is selected from the group consisting of pulmonary, buccal, sublingual, intranasal, rectal, and vaginal administration.

21. The method of claim 18 wherein the formulation is suitable for intraocular or conjunctival administration.

22. The method of claim 18 wherein the formulation is suitable for intracranial, intralesional, or intratumoral administration.

23. The method of claim 18 wherein the formulation is in an aqueous solution suitable for parenteral administration.

24. The method of claim 18 wherein the formulation is in a tablet or capsule suitable for oral administration.

25. The method of claim 18 wherein the formulation is in a suppository suitable for vaginal or rectal administration.

26. The method of claim 18 wherein the formulation is a dry powder suitable for pulmonary administration.

27. The composition of claim 1 wherein the taxane is paclitaxel.

28. The method of claim 11 wherein the taxane is paclitaxel.

29. The method of claim 17 wherein the taxane is paclitaxel.

30. The composition of claim 1 wherein the hydrophilic excipient is selected from the group consisting of water soluble polymers and sugars, and the wetting agent is a surfactant.

31. The method of claim 11 wherein the hydrophilic excipient is selected from the group consisting of water soluble polymers and sugars, and the wetting agent is a surfactant.

32. The method of claim 17 wherein the hydrophilic excipient is selected from the group consisting of water soluble polymers and sugars, and the wetting agent is a surfactant.

* * * * *